(12) United States Patent
Spearman (10) Patent No.: US 8,728,038 B2
(45) Date of Patent: May 20, 2014

(54) METHOD AND APPARATUS FOR ACCESSING BLOOD FROM AN IV CATHETER INSERTION DEVICE

(71) Applicant: William L. Spearman, Beaufort, SC (US)

(72) Inventor: William L. Spearman, Beaufort, SC (US)

(\*) Notice: Subject to any disclaimer, the term of this patent is extended or adjusted under 35 U.S.C. 154(b) by 0 days.

(21) Appl. No.: 13/706,324

(22) Filed: Dec. 5, 2012

(65) Prior Publication Data

US 2013/0172779 A1 Jul. 4, 2013

Related U.S. Application Data

(63) Continuation-in-part of application No. 13/340,445, filed on Dec. 29, 2011.

(51) Int. Cl.
*A61M 25/06* (2006.01)
*A61B 5/15* (2006.01)

(52) U.S. Cl.
CPC .......... *A61M 25/0693* (2013.01); *A61B 5/1422* (2013.01); *A61B 5/1416* (2013.01); *A61B 5/1405* (2013.01)
USPC ..................................... 604/168.01; 600/468

(58) Field of Classification Search
CPC .. A61B 5/1422; A61B 5/1405; A61B 5/1416; A61M 25/0693; A61M 25/0606
USPC ...................... 600/468, 578; 604/168.01, 900
See application file for complete search history.

(56) References Cited

U.S. PATENT DOCUMENTS

| | | | | |
|---|---|---|---|---|
| 5,368,029 A | * | 11/1994 | Holcombe et al. | 600/368 |
| 5,702,367 A | * | 12/1997 | Cover et al. | 604/110 |
| 5,743,872 A | * | 4/1998 | Kelly | 604/500 |
| 7,914,494 B2 | * | 3/2011 | Hiejima | 604/167.04 |
| 8,597,252 B2 | * | 12/2013 | Burkholz et al. | 604/168.01 |
| 2012/0016307 A1 | * | 1/2012 | Burkholz et al. | 604/168.01 |

\* cited by examiner

*Primary Examiner* — Nicholas Lucchesi
*Assistant Examiner* — Gerald Landry, II
(74) *Attorney, Agent, or Firm* — Kenneth A. Seaman (57) ABSTRACT

Disclosed is an apparatus and method for accessing blood located within a flash chamber of an IV catheter insertion device, the apparatus is separate from the IV catheter insertion device and sized to be attached to a structure of the IV catheter insertion device to secure it thereto. Once secured, movement of the plunger from its rearward position to a forward position presses on a flash plug to expel blood from a flash chamber of the IV catheter insertion device and out through the needle.

9 Claims, 7 Drawing Sheets

FIG. 9

METHOD AND APPARATUS FOR ACCESSING BLOOD FROM AN IV CATHETER INSERTION DEVICE

CROSS REFERENCE TO RELATED PATENT

The present invention is a continuation-in-part of my prior patent application, Ser. No. 13/340,445 filed Dec. 29, 2011 and entitled "IV Catheter Insertion Device and Method of Using It". The specification and drawings of that patent (which is sometimes referred to herein as the "System Patent") are hereby incorporated by reference into this patent.

BACKGROUND Of THE INVENTION

A patient admitted to a hospital, an outpatient treatment center, or an outpatient surgery center will have an intravenous (IV) catheter inserted for easy access for fluids and drugs to be administered to the patient. The IV catheter is typically inserted using an IV catheter insertion device, and some of these IV catheter insertion devices have become known in the industry as JELCOs after the name of one company which brought these insertion devices to market. In addition to placement of an IV catheter, it is frequently necessary for a sample of the patient's blood to be obtained—e.g., for testing, blood typing or other analysis. For many of these blood tests, only a small sample of blood is required. After the IV catheter has been inserted, the healthcare worker may obtain this blood sample by various means. One method would be to have the patient endure another needle stick either by a needle and syringe to draw an aliquot of blood, or by pricking the patient's finger with a lancet for a few drops of blood.

Several different types of intravenous (IV) catheter insertion devices currently are on the market. One such IV catheter insertion device is marketed by Smiths Medical under its ProtectIV trademark. This device can be seen represented by U.S. Pat. No. 5,000,740. This device uses a passive system to protect the user from needle stick injury. In its design, this device has a non-removable flash chamber. The invention described in this application provides a method and device to allow the user to access the blood within a flash chamber of such a device for testing.

Some have proposed to use some of the blood that remains within the JELCO or IV catheter insertion device after the IV catheter has been inserted in a patient for these simple blood tests. Most IV catheter insertion devices include an integrated flash chamber. Red blood appears within the flash chamber of an IV catheter insertion device as the operator inserts the needle of the IV catheter insertion device into the vein to show that the IV catheter has entered a vein. The operator watches the flash chamber continuing to fill with blood as the operator advances the IV catheter into the vein, thereby ensuring the IV catheter remains properly positioned within the vein. Usually the proximal end of the flash chamber is blocked by a flash plug. The flash plug typically includes a filter material that allows air to vent from the flash chamber as the blood or fluid fills the chamber, but prevents the blood or fluid from passing from the flash chamber. IV catheter insertion devices of the prior art may have one of two different types of flash plugs. One type of IV catheter insertion device, such as described in U.S. Pat. No. 5,000,740, has a fixed or non-removable flash plug. Another type of prior art IV catheter insertion device is seen in U.S. Pat. No. 4,917,671; this type of IV insertion device has a removable flash plug at the end of its flash chamber.

When an IV catheter has been placed within the vein, the remainder of the JELCO or IV catheter insertion device is removed from the patient. A small amount of the patient's blood remains within the flash chamber of the JELCO or IV catheter insertion device. By accessing the patient's blood from the flash chamber of the IV catheter insertion device, the operator may be able to avoid an additional needle stick to the patient. There are some known approaches to access blood in the flash chamber of an IV catheter insertion device. One IV catheter insertion device, such as U.S. Pat. No. 5,000,740 which is currently marketed by Smiths Medical under its ProtectIV trademark, offers a unique problem when trying to access the blood within the flash chamber since it has a non-removable flash plug. As such, users must adapt special methods if they wish to access the blood within the flash chamber. One such method to access this blood in an IV insertion device with a non-removable flash plug involves finding and using an external probe, such as a pen or a golf tee, to push the internal and non-removable flash plug within the flash chamber to expel blood from the flash chamber. The use of an external device such as a golf tee or pen is undesirable for several reasons. The external device must be stored some place that is easily accessible to the operator when the operator is ready to use it. The use of an external device is inefficient as the worker must look for or gather additional equipment when accessing the captured blood or fluid and replace the additional equipment for its next use, if the worker were to reuse any external probe or device (including a pen or a golf tee), cross-contamination may occur from one flash chamber to another, putting other patients and the healthcare worker at risk. In addition the user must align the external probe with the flash plug while pushing the device and flash plug forward within the flash chamber while at the same time keeping the tip of the needle over the correct spot on the testing strip.

In IV catheter insertion devices that have removable flash plugs, another prior art approach to access the blood in a flash chamber requires the healthcare worker to remove the flash plug, thereby opening the flash chamber to access the blood within the flash chamber for testing. This action may expose a healthcare worker needlessly to hazardous material (such as blood or other bodily fluid) that may spill from the flash chamber.

While various prior art methods may allow the healthcare worker to access the blood or fluid within the flash chamber of an IV catheter insertion device (or JELCO), these methods present an inefficient solution with undesirable aspects and limitations.

My System Patent provides a design of a complete IV insertion device in which blood can be accessed from the device. However, many institutions and professionals continue to use Jelco devices of the prior design, and it is desired to provide a way for them to access the blood which is located in the flash chamber for testing purposes.

The present invention addresses some of these undesirable limitations and aspects to provide an improved device and method for accessing blood from an IV catheter insertion device without the use of undesirable additional hardware and without unnecessary risks.

This new method and device will thereby increase the efficiency of the healthcare worker and reduce the hazardous exposure of bodily fluids to the workers and patients. Other disadvantages and limitation of the prior art systems will be apparent to those skilled in the art.

SUMMARY OF THE INVENTION

The present invention provides a system and method for providing a self-contained system for removing blood (or other fluid) from an IV catheter insertion device with a non-removable flash plug, such as the device sold under the ProtectIV trademark, in a controlled manner upon demand and with greater ease and less risk to the worker.

The present invention has the advantage of reducing the number of needle sticks to a patient by using blood or bodily fluid that has been collected within the IV catheter insertion device when the IV catheter is placed. That is, the fluid sample used for testing is a by-product of the use of the IV catheter insertion device.

Applicant teaches in this patent application that blood collected within the flash chamber of an intravenous catheter insertion device with a non-removable flash plug can be accessed with an attachable device which becomes attached to the IV catheter insertion device and allows access to blood within the flash chamber safely and efficiently. The blood or fluid thus collected can be used for analysis or testing without requiring the healthcare worker to inflict additional needle sticks to a patient.

It is desirable that any part of an IV catheter insertion device (or JELCO) be simple to make and maintain in a sterile condition. It is also desirable that the device be self-contained and not require additional tools, e.g., an external device like a golf tee or pen, in order to access the blood contained in the flash chamber.

It is also desirable that the operator be able to access the blood or fluid within the IV catheter insertion device without having to open the flash chamber or provide a separate device such as a golf tee or ballpoint pen which may not be sterile, thereby reducing the chance for exposure of hazardous material to the worker and patient.

It is further desirable that the device can be attached to the IV insertion device either during assembly of the IV insertion device, prior to insertion of the IV, or after the IV catheter is placed and the insertion device has been separated from the IV catheter.

The present invention overcomes the disadvantages and limitations of the prior art systems while providing a simple, yet effective, way of accessing the blood contained in the flash chamber of an IV catheter insertion device for testing and analysis without need for a golf tee or ballpoint pen.

The present invention overcomes some of the limitations and disadvantages of prior art systems.

The present invention provides a way of using an IV catheter insertion device of the prior art while being able to access blood which is located within the flash chamber for testing.

The present invention has the advantage that it works with flash plugs which are not removable (for example, as described in U.S. Pat. No. 5,000,740).

Other objects and advantages of the present invention will be apparent to those of ordinary skill in the art to which the present invention applies in view of the following detailed description of the preferred embodiment taken in conjunction with the accompanying drawings.

DETAILED DESCRIPTION OF THE PREFERRED EMBODIMENTS

A review of the workings of an intravenous catheter insertion device such as is sold under the ProtectIV trademark will allow the reader to better understand the present invention.

Figure 1:
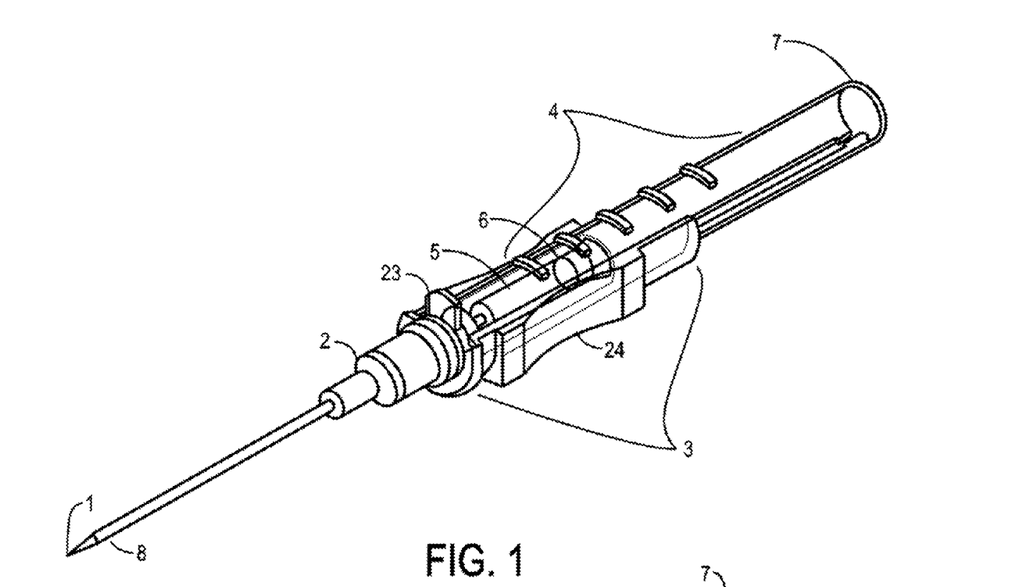
FIG. 1 is a perspective view of a prior art IV catheter insertion device suitable for use with the present invention, showing the device in its first position, prior to insertion of the IV catheter into a patient.
Figure 2:
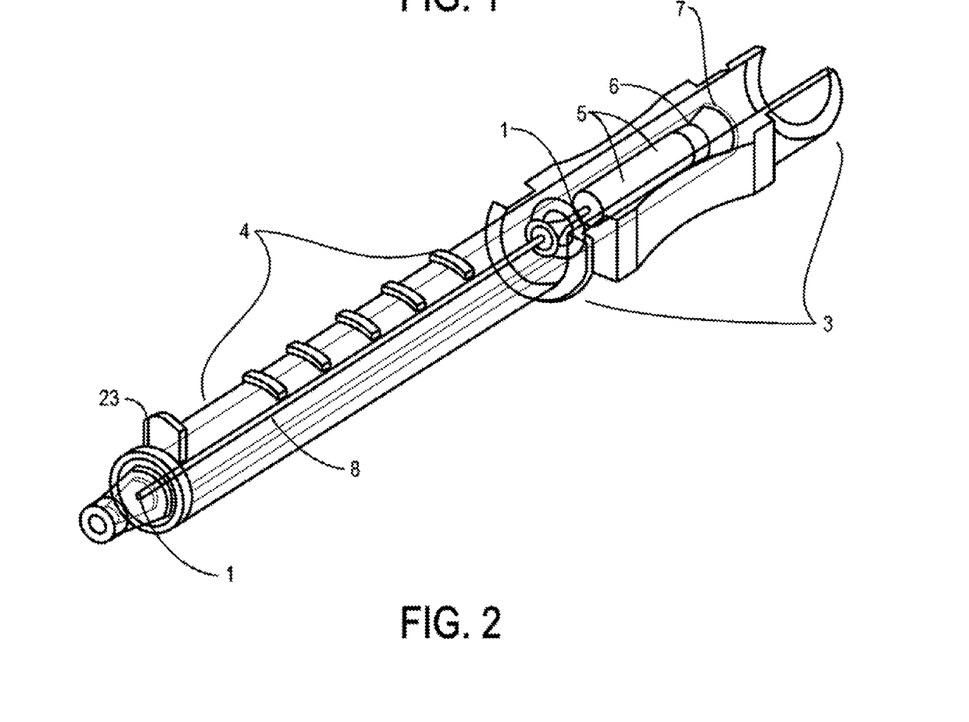
FIG. 2 is a perspective view of the prior art IV catheter insertion device of FIG. 1 in its second position, after placement of the IV catheter within the patient, when its needle is located within its protective tube.

FIG. 1 shows a ProtectIV IV catheter insertion device in its first position with a needle tip 1 prior to insertion of the IV catheter 2 into the patient. Using proper technique, the healthcare provider inserts the needle tip 1 through the skin and into the patient's vein. As with most current IV catheter insertion devices, as the tip of the needle 1 enters the patient's vein, blood flows from the needle tip 1 into the flash chamber 5 where the user can confirm access into the vein. The blood continues to flow into the flash chamber 5 as the IV catheter 2 advances into the vein. A flash plug 6 allows air to exit the flash chamber 5 but prevents the blood from exiting from the flash chamber 5. To advance the IV catheter 2 into the vein, the user pushes the finger tab 23 while holding finger grips 24 on the main carriage 3. This motion moves the protective tube 4 distally, which slides the IV catheter 2 off the needle and into the vein. At the same time, this motion slides the protective tube 4 distally to cover the needle 8 with its needle tip 1. The protective tube 4 slides through the main carriage 3 and over the needle and needle tip 1 until the tube locks in a second position (the insertion device without the IV catheter is shown in FIG. 2).

For a fuller understanding of the operation of one IV catheter insertion device and its mechanism for protecting the user from inadvertent needle sticks, see the specification and drawings of relevant patents such as U.S. Pat. No. 5,000,740, the specification and drawings of which are hereby Incorporated herein by reference.

Figure 3:
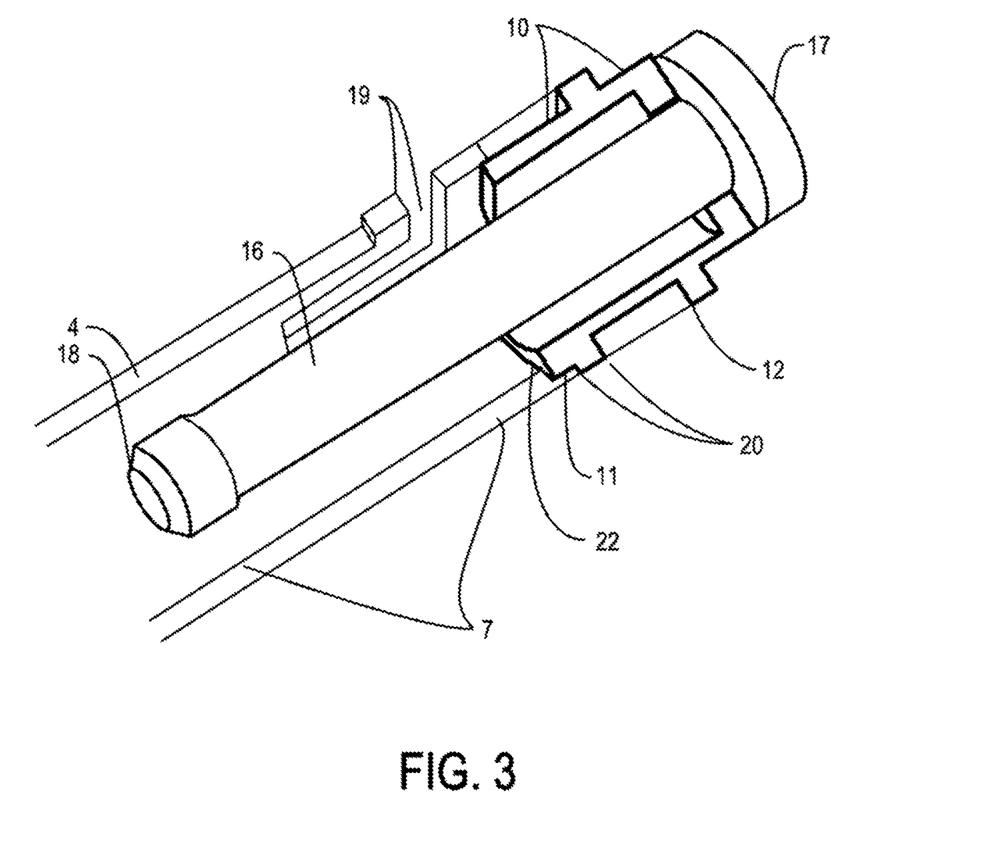
FIG. 3 is a cross-sectional view of a portion of the IV catheter insertion device of FIG. 1 with elements of the present invention shown, including a mounting member and a plunger.

As shown in FIG. 3, the present invention, in one embodiment, includes an endcap (sometimes also referred to herein as a "collar") 10 (perhaps seen best in FIG. 4) and a plunger 16. The assembly of the collar or endcap 10 with the plunger 16 is attached to a proximal end 7 of the protective tube 4 of the IV catheter insertion device. The IV catheter insertion device is shown in this FIG. 3 in its original position, such as prior to insertion of the IV catheter into a patient. One portion of the endcap 10 of the invention fits within the internal diameter of the proximal end 7 of the protective tube 4 of the IV catheter insertion device. The leading edge 22 of the endcap 10 slides within the proximal end 7 of the protective tube 4 until the protective tube contacts a retention ring 12 of the endcap 10. This retention ring 12 stops distal movement of the endcap 10 into the protective tube 4. In addition, toward the leading edge 22 of the endcap 10 is a flexible post 11 that snaps into an opening 20 in an anterior wall of the protective tube 4. This post 11 on the endcap 10 flexes to snap into the opening 20 to resist proximal movement of the endcap 10. With the retention ring 12 preventing distal movement and the post 11 resisting proximal movement, the endcap 10 is retained within the proximal end 7 of the protective tube 4. The plunger 16 includes an enlarged plunger handle portion 17 and a distal end or pusher portion 18 and is movably mounted within a central channel 14 of the endcap 10. The plunger 16 is freely moveable along its axis within the endcap 10 from a proximal position (FIG. 5) in which the distal end 18 of the plunger 16 is a closest to the top of the endcap 10 to a distal position (FIG. 6) in which the plunger handle portion 17 is adjacent to a proximal end 13 of the endcap 10.

Once the collar 10 of the present invention is attached to the proximal end 7 of the protective tube 4 when the IV catheter insertion device is in its original position, the plunger 16 can be pushed distally such that the shaft of the plunger 16 is enclosed within the protective tube 4. This position can be seen in FIG. 3. As seen in FIG. 3, the invention can be attached to the IV catheter insertion device while providing a low profile, with little change to the shape or size of the IV catheter insertion device so as not to interfere with the normal process of insertion of an IV catheter. That is, much of the collar and plunger assembly is within the protective tube when the assembly is mounted to the tube.

Figure 4:
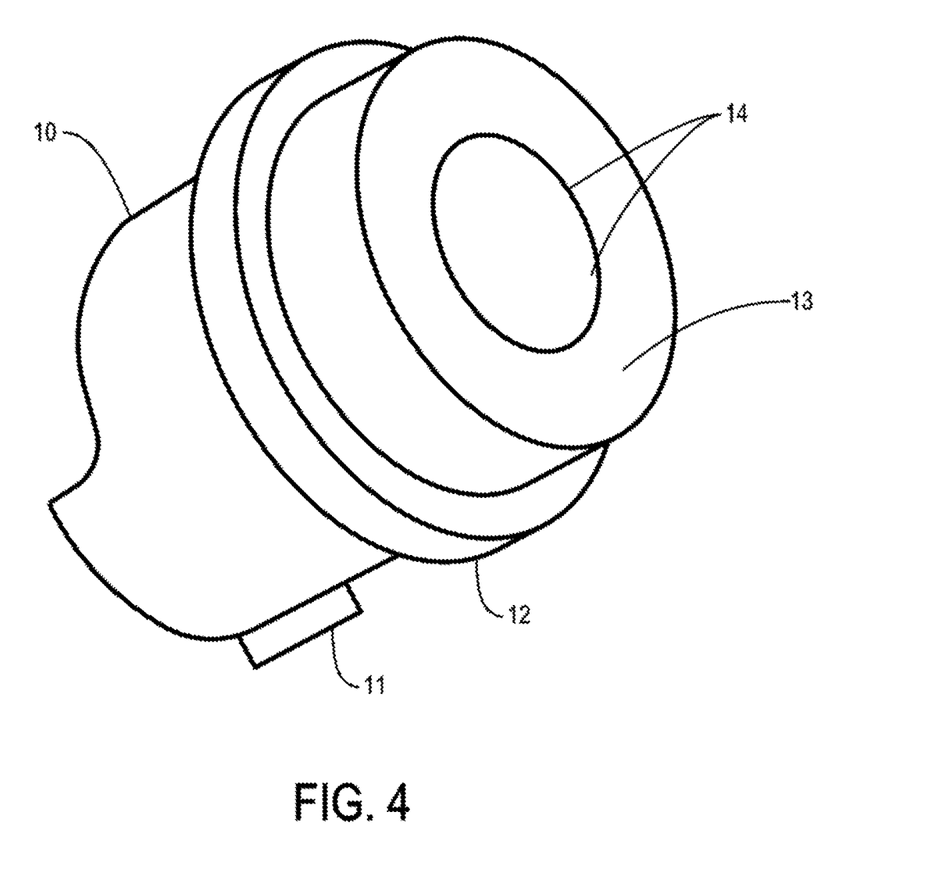
FIG. 4 is an enlarged, perspective view of the mounting member shown in FIG. 3.

FIG. 4 shows an enlarged perspective view of one form of the endcap or collar 10 useful in the present invention. The collar 10 includes the post 11 which is received in the aperture 20 of the protective tube 4. The retention ring 12 is a portion of larger diameter than the inner diameter of the tube 4 to limit how far the collar 10 can be inserted into the tube. The collar 10 has a central channel 14 through which the plunger is extends and the proximal end 13 of the endcap or collar 10. The endcap or collar 10 generally positions the plunger 16 to move along an axis which is generally aligned with the axis of the protective tube when the components are assembled.

Figures 5, 6:
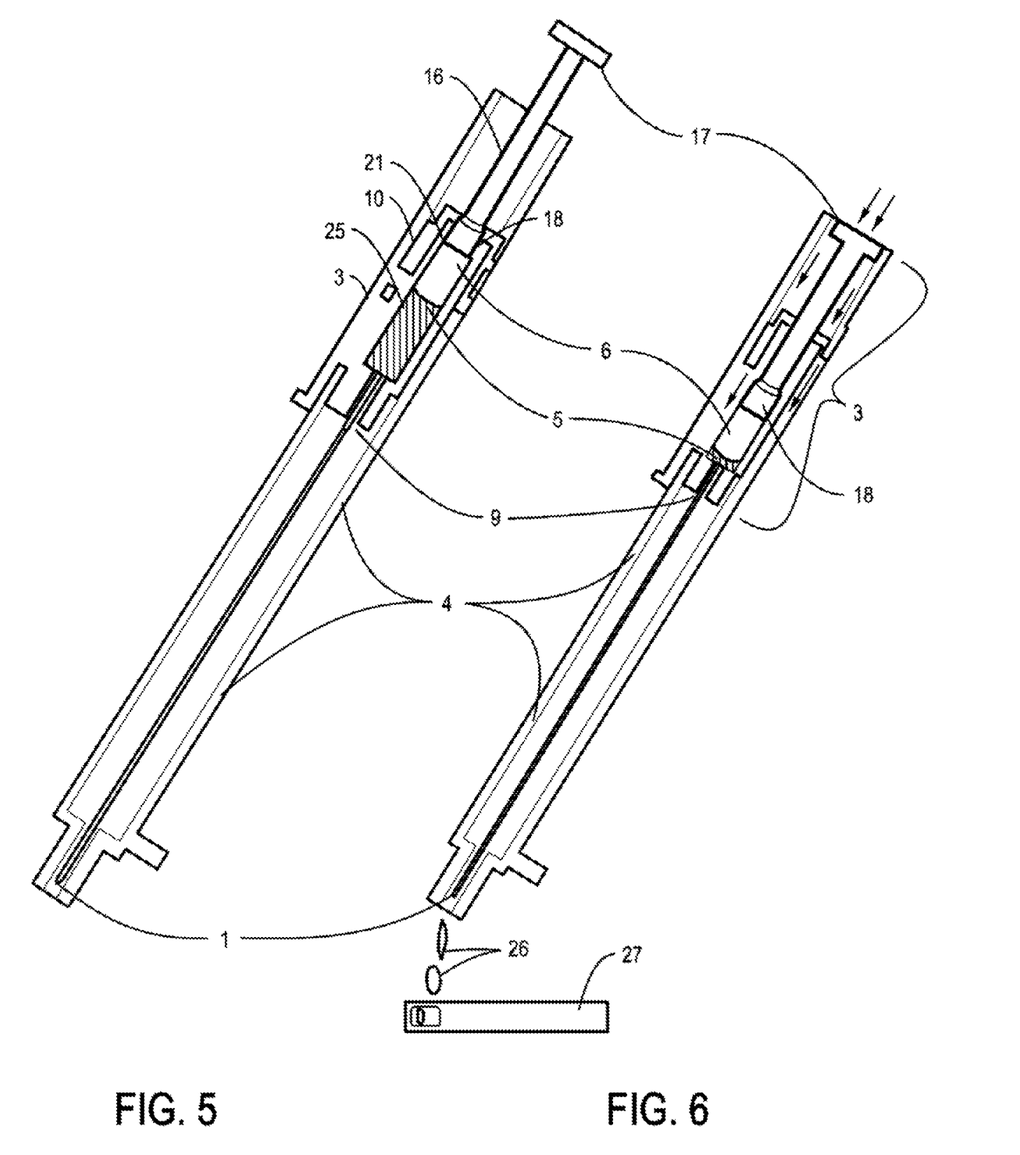
FIG. 5 is a cross sectional view of the IV catheter insertion device of the present invention with the plunger in its first or retracted position.
FIG. 6 is a cross sectional view of the IV catheter device of the present invention with its plunger advanced to a second or forward position to expel blood from the IV catheter insertion device's flash chamber.

The user would then use the IV catheter insertion device to place an IV catheter per normal technique. Once the user sees blood within the flash chamber 5, he advances the protective tube 4 by pushing the finger tab 23 distally. As the protective tube 4 moves distally, the collar 10 of the present invention moves distally with the tube 4 until the distal end 18 of the plunger 16 contacts the proximal end of the flash plug 6. Because the plunger 16 is freely moveable axially within the collar 10, contact with the flash plug 6 will move the plunger back or proximally as the protective tube 4 moves forward or distally. This forward (distal) movement of the protective tube 4 and backward (proximal) movement of the plunger 16 continues until the protective tube 4 locks into its second position (as shown in FIG. 5). A close up view of the protective tube 4 locked in its second position with the invention attached can be seen in FIG. 5. In this position, the distal end of the plunger 18 is positioned adjacent to the proximal end 21 of the flash plug 6. The proximal end of the plunger shaft 16 and the plunger handle 17 extend beyond the leading edge 29 of the main carriage 3.

After the user has secured the patient's IV catheter, the healthcare worker can use the invention to access the blood 25 within the flash chamber 5 for testing, see FIGS. 5 and 6. The healthcare worker would position the distal tip of the needle 1, now enclosed within the protective tube 4, over an appropriate blood receiving member such as a testing strip 27. The user would then push the handle 17 of the plunger 16 distally. The forward (distal) movement of the plunger 16 would then move the flash plug 6 distally within the flash chamber 5. This distal movement of the flash plug 6 will push the blood 25 from the flash chamber 5 through the needle 9 and out the needle tip 1 in the form of blood drops 26. The user can then direct the blood 26 expressed from the flash chamber 5 onto the testing strip 27. The user can then dispose of the IV catheter insertion device and the present invention together.

As the invention is attached to the IV catheter insertion device, the user does not need to look for an external probe (e.g., a separately-supplied and maintained golf tee or ball-point pen) or correctly position that probe to push blood from the flash chamber 5. In addition, the invention allows the user to express blood from the flash chamber 5 for testing without requiring the user to open the flash chamber 5 and exposing the healthcare worker to blood needlessly.

In this embodiment, the invention can be attached to an IV catheter insertion device in any one of several stages of use. The invention can be attached during the manufacture and/or assembly of the entire device and sterilized along with the IV insertion device. In addition, the invention can be attached by the user just prior to insertion of the IV catheter. The invention can even be attached after the IV catheter has been placed, when the IV catheter insertion device is locked in its second position as described above.

Figure 7:
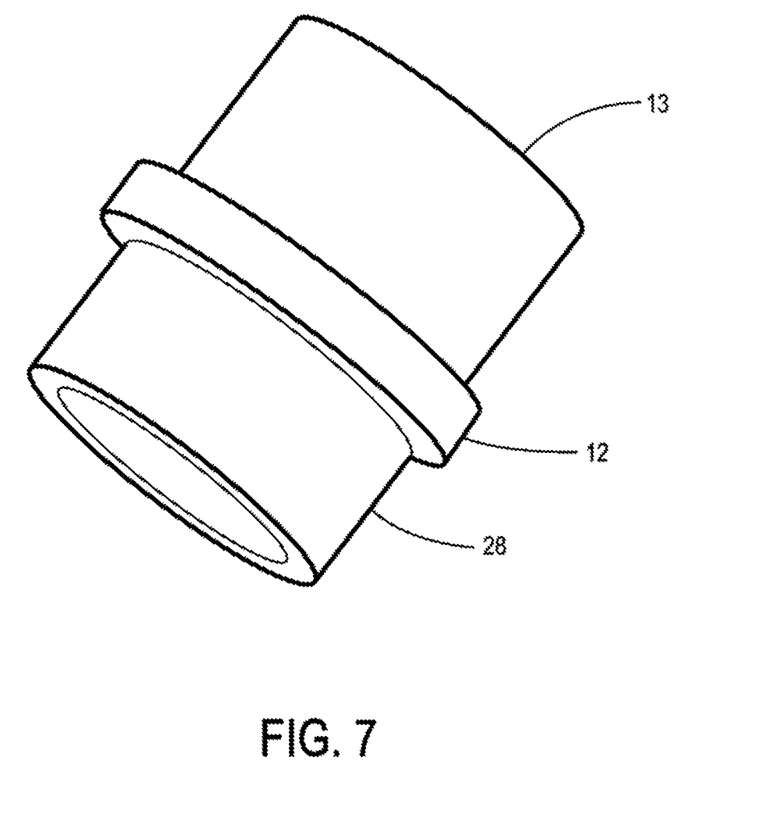
FIG. 7 is an enlarged, perspective view of an alternate embodiment of the mounting member of FIG. 4.
Figure 8:
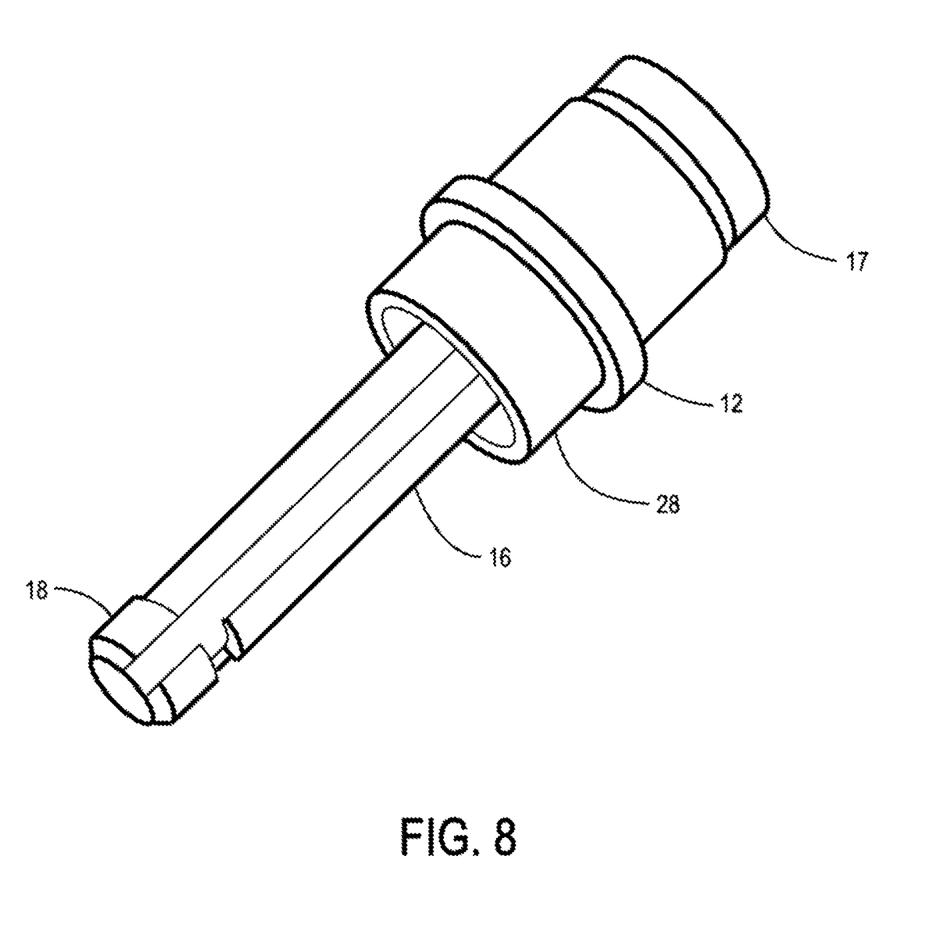
FIG. 8 is a perspective view of the mounting member of FIG. 7 with its plunger, showing the assembly similar to FIG. 3.
Figure 9:
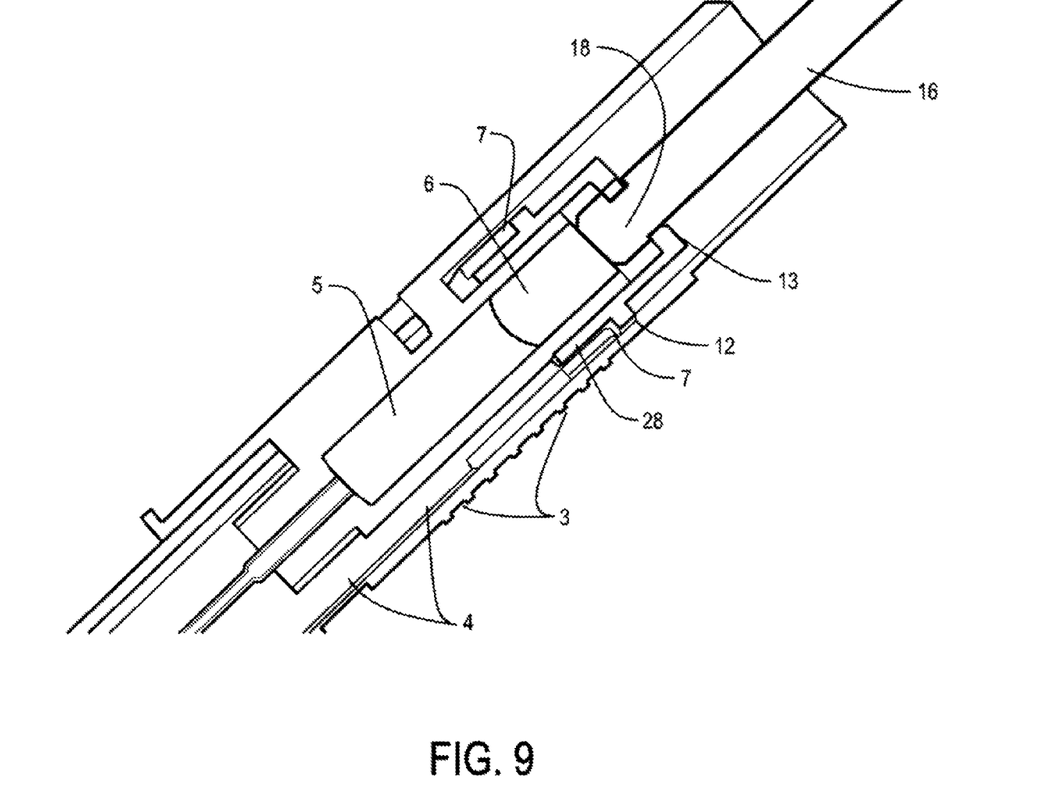
FIG. 9 is an enlarged, partial view of the IV catheter with the plunger and mounting member of FIGS. 7 and 8, similar to the view of FIG. 5.

In another embodiment which may be preferred in some situations, an endcap 10 may be fashioned without the locking post 11, such that the distal end of the endcap or collar 10 fits within the proximal end of the protective tube 7 and is held in place within the protective tube by a suitable retention force, such as by friction or another similar force (such as an adhesive). Such a system is shown in FIGS. 7-9, wherein the collar 10 includes the retention ring 12 and a distal surface 28 which is sized to be retained in frictional contact with the barrel when inserted therein to retain the collar 10 and the plunger 16 in its position within the protective barrel. FIG. 8 shows the assembly of the collar 10 with the plunger 16 having its handle 17 and its distal end or pusher portion 18. FIG. 9 shows portions of the assembly of FIGS. 7-8 mounted to the protective barrel 4. As shown in this view, the tip 18 is in contact with the flash plug 6 while the flash chamber 5 is shown. FIG. 8 also shows an optional arrangement on a shaft portion of the plunger 16 to allow the user to lock the plunger 16 in its extended position. If the user had not attached the present invention to the IV catheter insertion device prior to placing the IV catheter, the user might have a difficult time attaching the endcap 10 with the IV catheter device in its position of FIG. 2. With the shaft of the plunger 16 locked in its extended position, the user could manipulate the endcap 10 into the proximal end 7 of the protective tube 4 of the IV. The user could then unlock the shaft of the plunger 16 and express blood from the flash chamber 5 by advancing the plunger 16 using its handle 17.

In another embodiment, the invention may or may not have the following optional features which may be desirable in some applications. The collar or endcap 10 may have a locking post that is of graduated height. That is, the distal or forward edge of the locking post could be even with the distal or leading edge of the collar 10. The height of the locking post would gradually increase to a height necessary to secure the assembly of the collar 10 and plunger 16 within the appropriate hole in the protective tube 4 of the IV catheter insertion device. In addition, in this alternate embodiment, the device may have slits or openings on either side of its locking post. These openings will allow the section with the locking post to flex inward slightly as the collar or endcap 10 is inserted within the proximal end 7 of the protective tube 4. This inward flex will continue until the locking post snaps into position within the hole in the protective tube 4.

Of course, many modifications and adaptations of the present invention are possible without departing from its spirit. Further, some of the features of the present invention may be used to advantage without the corresponding use of other features. For example, the present invention has been discussed in the context of an annular mounting device which fits within a round opening in the barrel of the IV catheter insertion device. But, the IV catheter insertion device itself does not have to be round, and the mount need not be round nor mounted within the barrel. Further, the mounting such as the collar may be attached or otherwise secured to the barrel in another manner, such as a press-fit, or by a securing device, such as a through pin, or an adhesive. While the design has been disclosed in the context of an projection of the collar fitting into an aperture in the protective tube, a design in which the collar includes an aperture and the tube has a complementary projection would work as well. Thus, it will be appreciated that the foregoing description of the best mode of the present invention is provided solely for illustrative purposes and not in limitation of the present invention which is defined solely by the following claims.

Having thus described the invention, what is claimed is:

1. A method of accessing blood in a flash chamber of an IV insertion device having a barrel with a flash plug mounted adjacent to the flash chamber, the steps of the method comprising:
   providing a movable plunger and a plunger mounting structure surrounding the plunger, said movable plunger and plunger mounting structure being separate from the IV catheter insertion device;
   mounting the plunger mounting structure to the barrel of the IV insertion device with the plunger adjacent the flash plug within the barrel; and
   moving the plunger with respect to the barrel and the flash plug to press on the flash plug to expel blood from the flash chamber for testing.

2. A method of accessing blood including the steps of claim 1 and further including the step of providing a projecting post on the plunger mounting structure and snapping the projecting post into an aperture in the barrel of the IV catheter insertion device.

3. A method of accessing blood including the steps of claim 2 and further including the step of using the plunger to press on the flash plug to compress the flash chamber and thereby expel blood from the flash chamber.

4. An apparatus far accessing blood in a flash chamber of an intravenous catheter insertion device having a barrel with a flash plug movably mounted therein adjacent to a flash chamber, the apparatus comprising:
   a mounting collar secured to the barrel; and
   a plunger mounted within the mounting collar and movable between a first position and a second position, the first position not pressing on the flash plug and the flash chamber to expel blood from the flash chamber and the second position being in contact with the flash plug to move the flash plug to compress the flash chamber and expel blood for testing when the plunger is moved from its first position to its second position.

5. An apparatus including the components of claim 4 wherein the apparatus further includes a flexible post carried on the collar and sized and positioned to fit within a complementary aperture on the barrel for securing the collar to the barrel.

6. An apparatus including the components of claim 5 further including an enlarged portion on the collar, said enlarged portion on the collar being larger than the internal diameter of the barrel to limit the travel of the collar into the barrel.

7. The apparatus of claim 4 wherein the mounting collar and the plunger are mounted within the barrel to provide a reduced profile of the apparatus.

8. The apparatus of claim 4 wherein the flash plug is not removable from the barrel.

9. The apparatus of claim 4 wherein the mounting collar aligns the plunger generally with the barrel so that the plunger advances along an axis of the barrel as it moves from its first position to its second position.

* * * * *